US007301029B2

(12) United States Patent
Kuwabara et al.

(10) Patent No.: US 7,301,029 B2
(45) Date of Patent: Nov. 27, 2007

(54) BIPYRIDINE DERIVATIVES

(75) Inventors: Hirokazu Kuwabara, Hiratsuka (JP); Takayuki Sonoda, Hiratsuka (JP); Hiromitsu Saitoh, Hiratsuka (JP); Hidehiro Arai, Hiratsuka (JP)

(73) Assignee: Fujifilm Finechemicals Co., Ltd., Tokyo (JP)

( * ) Notice: Subject to any disclaimer, the term of this patent is extended or adjusted under 35 U.S.C. 154(b) by 258 days.

(21) Appl. No.: 10/916,530

(22) Filed: Aug. 12, 2004

(65) Prior Publication Data
US 2005/0085642 A1 Apr. 21, 2005

(51) Int. Cl.
*C07D 401/00* (2006.01)
*C07D 213/22* (2006.01)
*C07D 213/26* (2006.01)

(52) U.S. Cl. ........................ 546/256; 546/257; 546/258

(58) Field of Classification Search ................. 546/257, 546/256, 258
See application file for complete search history.

(56) References Cited

U.S. PATENT DOCUMENTS

| 5,834,471 | A | * | 11/1998 | Duckworth et al. | ... 514/252.13 |
| 6,359,134 | B1 | * | 3/2002 | Tawada et al. | ............. 544/333 |
| 6,603,007 | B1 | | 8/2003 | Shintou | |
| 6,747,023 | B1 | * | 6/2004 | Kobayashi et al. | ...... 514/224.2 |
| 2005/0222410 | A1 | * | 10/2005 | Stokes et al. | ................ 544/124 |

FOREIGN PATENT DOCUMENTS

WO        WO009480        *  2/2000

OTHER PUBLICATIONS

Stokes et al, 'Preparation of amides as inhibitors of histone deacetylase', (2003) CA 139:381375.*
Duckworth et al, 'Preparation of pipetazinylphenylcarboxamine derivatives as 5-HT1D receptor antagonists' (1995) CA 122:290891.*
Tawada et al, 'Preparaton of 1-benzoyl-4-naphthalenesulfonylpiperazines and related compounds as inhibitors of activated coagulation factorX' (1998) CA 130:38404.*
Ishikura et al, 'A novel synthesis of 4-aryl- and 4-heteroarylpyridines via diethyl(4-pyridyl)borane' (1987) CA 106:32776.*
Seki et al, 'Photo-arylation. Part V. Photoreacton of 4-iodopyridine with heteroaroamatics', (1986) CA 105:208737.*
Alegria et al, 'Preparationof N-heterocyclyl-substituted aminothiazole derivatives as protein kinase inhibitors' CA 141:243546 (2004).*
Kanno et al, 'Preparation of diamides and their use as factor Xa inhibitors and blood coagulation inhibitors for oral treatment of thrombotic diseases', (2004) CA 141:156930.*
Bakthavatchalam et al, 'Substituted biphenyl-4-carboxylic acid arylamide analogues as VR1 receptors modulators' (2004) CA 141:89019.*
Ito et al, 'Sulfur heterocycle-condensed pyrimidinedione derivatives, prodrugs of them, JNK inhibitors containing them, and pharmaceuticals containing them' (2004) CA 141:47322.*
Caulkett, 'Preparation of heterocyclic derivatives as inhibitors of factor Xa' (2000) CA 133:177190.*

* cited by examiner

*Primary Examiner*—Thomas McKenzie
*Assistant Examiner*—Raymond Covington
(74) *Attorney, Agent, or Firm*—Sughrue Mion, PLLC

(57) ABSTRACT

The invention provides a bipyridine derivative useful as an intermediate for pharmaceutical products, agricultural chemicals, electrophotographic photosensitive materials, dyes and the like, which is a bipyridine derivative represented by the general formula (I) and a salt thereof:

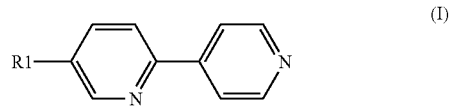

(I)

wherein R1 represents an alkyl group with 2 to 20 carbon atoms having a substituent, substituted or unsubstituted aminomethyl group, trifluoromethyl group, substituted or unsubstituted thiomethyl group, substituted or unsubstituted alkenyl group, substituted or unsubstituted alkoxy group, substituted or unsubstituted aryloxy group, substituted carbonyl group, substituted sulfonyl group, unsubstituted or monosubstituted carbamoyl group, unsubstituted or monosubstituted sulfamoyl group, substituted or unsubstituted thiol group, unsubstituted or monosubstituted amino group, substituted carbonylamino group, substituted or unsubstituted ureido group, nitro group, cyano group, formyl group or an equivalent thereof, iodine atom or fluorine atom.

3 Claims, No Drawings

BIPYRIDINE DERIVATIVES

BACKGROUND OF THE INVENTION

1. Field of the Invention

The present invention relates to a bipyridine derivative functioning as an important intermediate in the fields of for example pharmaceutical products, agricultural chemicals, catalyst ligands, combinatorial chemistry, organic electroluminescence devices, electron charge transfer substances, electrophotograpic photosensitive substances and dyes.

2. Description of the Related Art

Use of bipyridine derivatives mainly including 2,4'-bipyridine is developed for a wide variety of fields. The derivatives draw attention as very attractive compounds. In the fields of recent pharmaceutical and agricultural chemicals, for example, the derivatives are used as α1A-selective antagonists (Canadian Journal of Chemistry, 2002, Vol. 80, No. 6, pp. 646-652).

In the field of ligands, additionally, numerous reports have been issued including a report about the use thereof as a ligand for ruthenium metal (Canadian Journal of Chemistry, 2002, Vol. 80, No. 6, pp. 646-652), as ligands for copper and cadmium (Journal of Organometallic Chemistry, 2002, Vol. 655, pp. 31-38) and as a ligand for manganese (II), cobalt (II), nickel (II) or copper (II) (Polish Journal of Chemistry, 2002, Vol. 76, No. 7, pp. 1047-1052).

As organoelectroluminescence devices, for example, there are organoelectroluminescent materials using highly luminescent organic iridium complexes and an example of the use thereof for organoelectroluminescence devices (Official gazette of JP-A-2003-147345).

In the photosensitive field, the use thereof for the purpose of providing a silver halide photosensitive material with high sensitivity, improved storability of fresh samples and less contamination of dyes is reported (Official gazette of JP-A-2001-152044).

As dye enhancers, a report tells about a photoelectrochemical battery of dye enhancement type and with less electricity generation loss as well as the usefulness of a bipyridine-carboxylic acid-ruthenium (II) complex hydrate as a dye enhancer for photoelectrochemical battery of dye enhancement type and with smaller inner resistance (Official gazette of JP-A-2003-163037).

In a wide variety of fields, additionally, as many as 200 patents and references report the assessment of their usefulness (Journal of Thermal Analysis and Calorimetry, 2000, Vol. 60, No. 1, pp. 145-150).

SUMMARY OF THE INVENTION

It is an object of the invention to provide a bipyridine derivative functioning as an important intermediate in the fields of for example pharmaceutical products, agricultural chemicals, catalyst ligands, combinatorial chemistry, organoelectroluminescence devices, electron charge transfer substances, electrophotographic photosensitive substances and dyes.

The inventors made investigations so as to achieve the object. The inventors made a success in obtaining a novel bipyridine derivative useful as an important intermediate in the fields of for example pharmaceutical products, agricultural chemicals, catalyst ligands, combinatorial chemistry, electrophotographic photosensitive substances and dyes. Thus, the invention has been achieved.

The invention includes the following aspects.

1. A bipyridine derivative represented by the general formula (I) and a salt thereof:

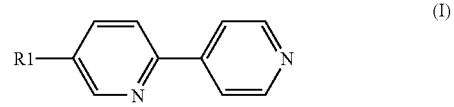

wherein R1 represents an alkyl group with 2 to 20 carbon atoms having a substituent, substituted or unsubstituted aminomethyl group, trifluoromethyl group, substituted or unsubstituted thiomethyl group, substituted or unsubstituted alkenyl group, substituted or unsubstituted alkoxy group, substituted or unsubstituted aryloxy group, substituted carbonyl group, substituted sulfonyl group, unsubstituted or monosubstituted carbamoyl group, unsubstituted or monosubstituted sulfamoyl group, substituted or unsubstituted thiol group, unsubstituted or monosubstituted amino group, substituted carbonylamino group, substituted or unsubstituted ureido group, nitro group, cyano group, formyl group or an equivalent thereof, iodine atom or fluorine atom).

2. The bipyridine derivative and a salt thereof described above in 1, wherein R1 represents an alkyl group with 2 to 20 carbon atoms having a substituent, an alkoxy group with 1 to 20 carbon atoms, which may have a substituent, an alkylthio group with 1 to 20 carbon atoms, which may have a substituent, unsubstituted or monosubstituted amino group, nitro group, formyl group, cyano group, unsubstituted or monosubstituted carbamoyl group or substituted carbonylamino group.

3. The bipyridine derivative and a salt thereof described above in 1, wherein R1 represents unsubstituted amino group, nitro group, formyl group, cyano group, unsubstituted carbamoyl group or carbonylamino group substituted with a lower alkyl group.

In accordance with the invention, a pyridine derivative useful as an intermediate for pharmaceutical products, agricultural chemicals, electrophotographic photosensitive substances, dyes and the like can be provided.

DETAILED DESCRIPTION OF THE INVENTION

The invention is now described in detail hereinbelow.

In accordance with the invention, R1 in the formula (I) represents an alkyl group with 2 to 20 carbon atoms having a substituent, substituted or unsubstituted aminomethyl group, trifluoromethyl group, substituted or unsubstituted thiomethyl group, substituted or unsubstituted alkenyl group, substituted or unsubstituted alkoxy group, substituted or unsubstituted aryloxy group, substituted carbonyl group, substituted sulfonyl group, unsubstituted or monosubstituted carbamoyl group, unsubstituted or monosubstituted sulfamoyl group, substituted or unsubstituted thiol group, unsubstituted or monosubstituted amino group, substituted carbonylamino group, substituted or unsubstituted ureido group, nitro group, cyano group, formyl group or an equivalent thereof, iodine atom or fluorine atom.

The alkyl group with 2 to 20 carbon atoms having a substituent as represented by R1 in the general formula (I) is an alkyl group with 2 to 20 carbon atoms, where at least one substituent is bound.

The substituent which the alkyl group with 2 to 20 carbon atoms may have includes for example amino group, halogen atoms, thiol group, aryl group, hetero-ring residues, and alkoxy group. These groups may additionally have substituents.

The aminoalkyl group as the substituted alkyl group in R1 includes for example aminoethyl, aminododecyl, aminooctadecyl, N-methylaminoethyl, N-methylaminohexyl, N-methylaminohexadecyl, N,N-diethylaminoethyl, N,N-diethylaminooctyl, N,N-diethylaminohexadecyl, N-phenylaminoethyl, N-phenylaminotetradecyl, N,N-diphenylaminoethyl and N,N-diphenylaminononyl.

The halogenated alkyl group as the substituted alkyl group in R1 is preferably fluoroalkyl group and more preferably perfluoroalkyl group, and specifically includes pentafluoroethyl, tridecafluorohexyl, and tritriacontafluorohexadecyl.

The arylalkyl group as the substituted alkyl group in R1 includes for example phenylethyl, phenyldecyl and naphthylpropyl.

Thioalkyl group as the substituted alkyl group in R1 includes for example methylthioethyl, methylthiopropyl, ethylthiobutyl, methylthiopentyl, propylthiohexyl, methythioheptyl, phenylthiooctyl, methylthiononyl, ethylthiodecyl, propylthiododecyl and phenylthiohexadecyl.

The hetero ring which the substituted alkyl group in R1 may have includes for example thiophene, furan, pyran, pyridine, pyrrole, pyrazine, azepine, azosine, azonine, azesine, oxazole, thiazole, pyrimidine, pyridazine, triazine, triazole, tetrazole, imidazole, pyrazole, morpholine, thiomorpholine, piperidine, piperazine, quinoline, isoquinoline, indole, isoindole, quinoxaline, phthalazine, quinolizine, quinazoline, quinoxaline, naphthyridine, chromene, benzofuran, and benzothiophene. Preferably, the hetero ring is a 5-membered or 6-membered hetero ring.

The alkoxyalkyl group as the substituted alkyl group in R1 includes for example methoxyethyl, ethoxyethyl, methoxypropyl, methoxyhexyl, ethoxyoctyl, butoxyhexadecyl and methoxyoctadecyl.

The substituted aminomethyl group in R1 includes for example N-methylaminomethyl, N-ethylaminomethyl, N-hexylaminomethyl, N-phenylaminomethyl, N,N-dimethylaminomethyl, N,N-diethylaminomethyl, N,N-dioctylaminomethyl, and N, N-diphenylaminomethyl.

The substituted thiomethyl group as R1 includes for example methylthiomethyl, butylthiomethyl, dodecylthiomethyl, and phenylthiomethyl.

The alkenyl group as R1 includes for example linear, branched or cyclic alkenyl groups such as vinyl, allyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, icosenyl, hexadienyl, and dodecatrienyl. The alkenyl group as R1 preferably has 2 to 20 carbon atoms.

The alkoxy group as R1 includes for example methoxy, ethoxy, propoxy, butoxy, pentyloxy, hexyloxy, heptyloxy, octyloxy, nonyloxy, decyloxy, dodecyloxy, and octadecyloxy. The alkoxy group as R1 preferably has one to 20 carbon atoms.

The aryloxy group in R1 includes for example phenoxy, and naphthyloxy.

The substituted carbonyl group in R1 includes for example acetyl, propanoyl, butanoyl, pentanoyl, hexanoyl, heptanoyl, benzoyl and naphthoyl.

The substituted sulfonyl group as R1 includes for example methylsulfonyl, ethylsulfonyl, propylsulfonyl, butylsulfonyl, pentylsulfonyl, hexylsulfonyl, heptylsulfonyl, octylsulfonyl, phenylsulfonyl and naphthylsulfonyl.

The monosubstituted carbamoyl group in R1 includes monosubstituted carbamoyl groups substituted with one group, for example N-methylcarbamoyl, N-(tert-butyl)carbamoyl, N-dodecylcarbamoyl and N-phenylcarbamoyl.

The monosubstituted sulfamoyl group in R1 includes monosubstituted sulfamoyl groups substituted with one group, for example N-ethylsulfamoyl, N-(iso-hexyl)sulfamoyl, N-hexadecylsulfamoyl and N-phenylsulfamoyl.

The substituted thiol group in R1 includes for example methylthio, ethylthio, propylthio, butylthio, pentylthio, hexylthio, heptylthio, octylthio, nonylthio, decylthio, dodecylthio, hexadecylthio, phenylthio, naphthylthio, 2-pyrimidylthio, and 4-pyridylthio.

The monosubstituted amino group in R1 includes monosubstituted amino group groups substituted with one group, for example N-methylamino, N-ethylamino, N-octylamino, N-hexadecylamino, and N-phenylamino.

The substituted carbonylamino group in R1 includes for example acetylamino, ethylcarbonylamino, tert-butylcarbonylamino, n-octylcarbonylamino, n-hexadecylcarbonylamino, benzoylamino, naphthoylamino, methoxycarbonylamino, ethoxycarbonylamino, n-octyloxycarbonylamino and n-hexadecyloxycarbonylamino.

The substituted ureido group in R1 includes for example N-methylureido, N-(iso-butyl)ureido, N-hexylureido, N-octadecylureido, and N-phenylureido.

The equivalent of formyl group in R1 includes for example di-alkoxymethyl group such as dimethoxymethyl and diethoxymethyl; trialkoxymethyl group such as trimethoxymethyl and triethoxyethyl; dialkylthiomethyl group such as dimethylthiomethyl and diethylthiomethyl; trialkylthiomethyl group such as trimethylthiomethyl and triethylthiomethyl; 1,3-dioxolanyl group; and 1,3-dithiolanyl group.

These substituents may additionally have any substituents with no specific limitation. The additional substituents include for example but are not limited to alkyl, alkenyl, phenyl, alkoxy, phenoxy, benzyloxy, amino, alkylthio, phenylthio and halogen atom.

R1 is preferably an alkyl group with 2 to 20 carbon atoms and with substituents, an alkoxy group with one to 20 carbon atoms, which may or may not have a substituent, an alkylthio group with one to 20 carbon atoms, which may or may not have a substituent, unsubstituted or monosubstituted amino group, nitro group, formyl group, cyano group, unsubstituted or monosubstituted carbamoyl group or substituted carbonylamino group. More preferably, R1 is unsubstituted amino group, nitro group, formyl group, cyano group, unsubstituted carbamoyl group or carbonylamino group substituted with a lower alkyl group.

The compound represented by the general formula (I) in accordance with the invention can be converted to a salt by known methods.

Herein, the salt includes for example alkali metal salts, alkali earth metal salts, ammonium salts, ammine salts and acid addition salts.

Appropriate examples of them include salts with alkali metals such as potassium and sodium; salts with alkali earth metals such as calcium and magnesium; salts with ammonium such as tetramethylammonium; salts with organic amines such as triethylamine, methylamine, dimethylamine, cyclopentylamine, benzylamine, phenetylamine, piperidine, monoethanolamine, diethanolamine, tris(hydroxymethyl) aminomethane, lysine, arginine, and N-methyl-D-glucamine.

Appropriate acid addition salts include for example inorganic acid salts such as hydrochloride salt, hydrobromide salt, hydroiodide salt, sulfate salt, phosphate salt, and nitrate salt; organic acid salts such as acetate salt, lactate salt, tartrate salt, benzoate salt, citrate salt, methanesulfonate salt, ethanesulfonate salt, benzenesulfonate salt, toluenesulfonate salt, isethionate salt, glucuronate salt, and gluconate salt.

Specific examples of the compound represented by the general formula (I) are now shown below. However, the invention is not limited to these compounds.

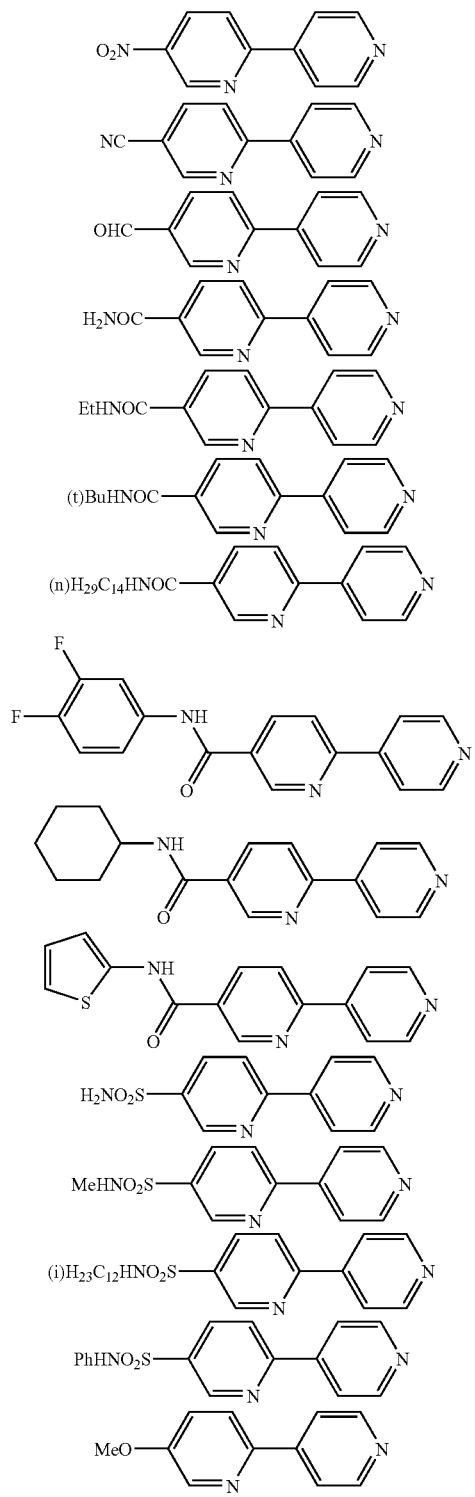

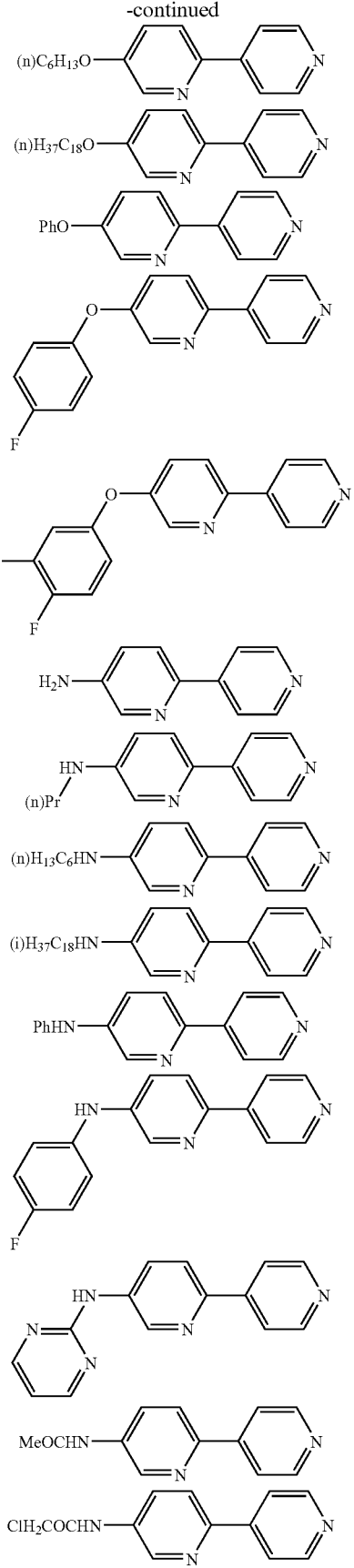

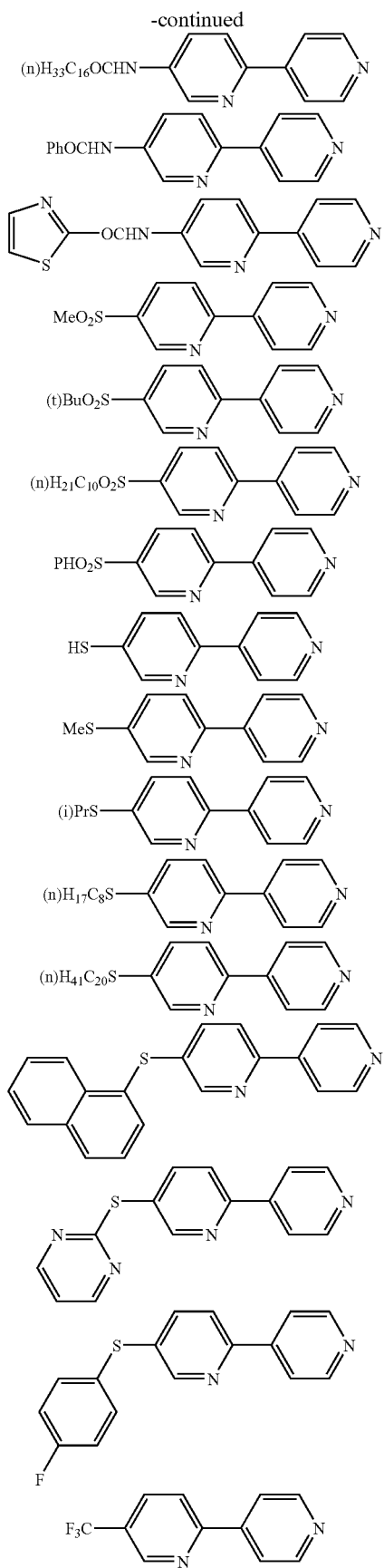
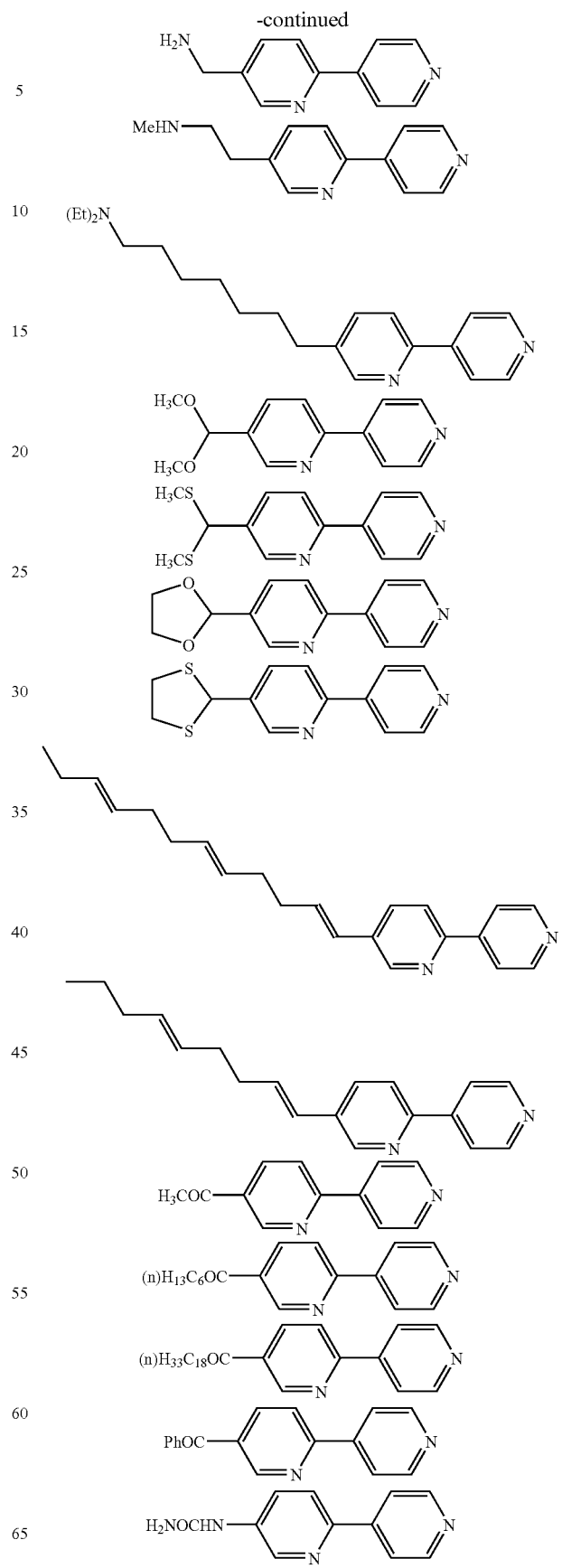

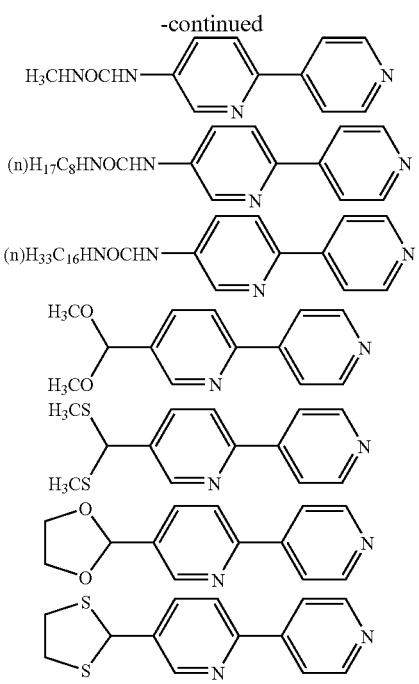

The method for producing the compound represented by the general formula (I) is now described below. The bipyridine derivative of the invention can be produced synthetically by known methods, for example methods described in JP-A-2000-355580, JP-A-2001-261646, JP-A-2001-261647, JP-A-2001-261653 and the like. As one example, 4-acetylpyridines and 3-amino-2-propenals react together; then, the resulting reaction product reacts with ammonia or an ammonium salt to produce the compound. One example of the reaction schemes is shown. However, the invention is never limited to the example.

for example J. AM. Chem. Soc., 103, 3030 (1981); J. Chem. Soc. PERKINTRANS. I, 333 (1988); Collect. Czech. Chem. Commun., 61,1637 (1996); and Collect. Czech. Chem. Commun., 49, 2602 (1984).

Further, 4-acetylpyridines represented by the general formula (II) as a raw material (abbreviated as 4-aceylpyridines hereinbelow) can readily be available as commercial products. Acyl group can be introduced in pyridine compounds by Friedel-Crafts reaction (J. Org. Chem., 38, 1445 (1973); J. Am. Chem. Soc., 79, 1445 (1957); J. Am. Chem. Soc., 84, 813 (1962)).

In accordance with the invention, a base is preferably allowed to exist during the condensation reaction between 4-acetylpyridines and 3-amino-2-propenals. As the base for use in accordance with the invention, any base may be usable. Generally, metal alkoxides such as potassium t-butoxide, sodium t-butoxide, and sodium ethoxide; inorganic bases such as sodium hydride, metal sodium, sodium hydroxide and potassium hydroxide; organic bases such as triethylamine, 1,8-diazabicyclo[5.4.0]undec-7-ene and diisopropylamine are used.

Preferably, the base is potassium t-butoxide, sodium methoxide and sodium hydride. More preferably, the base is potassium t-butoxide. Additionally, two or more bases may be mixed and used. In case of using bases in mixture, the mix ratio may be appropriately determined. The amount of the base to be used is within a range of 0.5- to 5-fold moles, preferably 0.5- to 1.5-fold moles, more preferably 0.8- to 1.2-fold moles to the amount of 3-amino-2-propenals.

The reaction is conducted at a temperature of −78 to 200° C., preferably within a range of −30 to 100° C., more preferably within a range of −10 to 40° C. Generally, these reactions are on completion within 24 hours. In many cases, the elimination of the raw materials can be verified in 10 minutes to 12 hours.

After 4-acetylpyridines react with 3-amino-2-propenals as described above, a cyclization reaction is carried out. In case that R3 and R4 are both hydrogen atom in the general

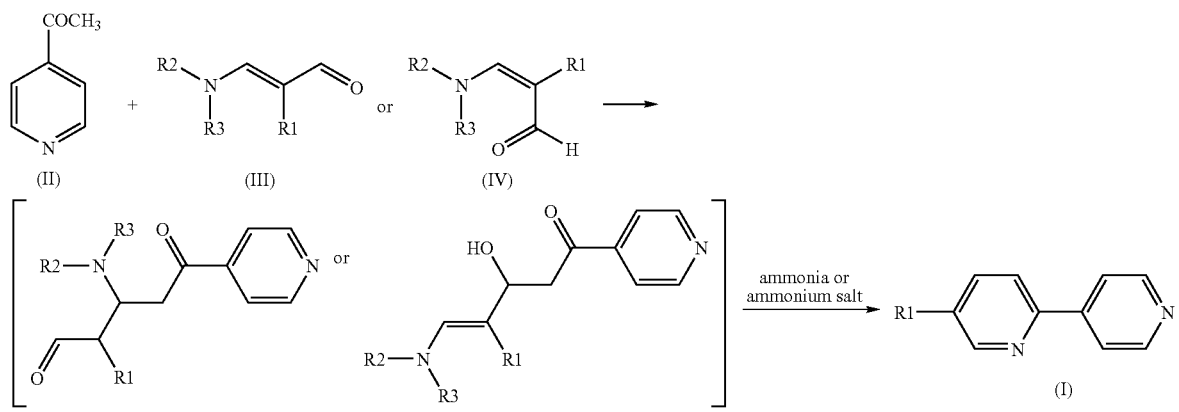

In the scheme, R1 has the same meanings as described above. R2 and R3 independently represent an appropriate substituent.

3-Amino-2-propenals represented by the general formula (III) or (IV) (abbreviated as 3-amino-2-propenals hereinafter) for use in accordance with the invention can readily be available as commercial products or can readily be synthetically prepared in a simple manner by a method described in formula (III), the reaction proceeds with no addition of ammonia or an ammonium salt. In case that at least one of R3 and R4 is not hydrogen atom, however, ammonia or an ammonium salt is added as a nitrogen atom source for the pyridine ring. Any type of ammonia or an ammonium salt may be used as such. Generally, ammonia gas, ammonium chloride, ammonium acetate and ammonium formate are used. Ammonium chloride, ammonium acetate and ammonium formate are preferable, and ammonium acetate is more preferable. As to the amounts of them for use, the reaction is carried out satisfactorily within a range of 1- to 30-fold moles, preferably 1- to 15-fold moles, more preferably 3- to 6-fold moles per one mole of 4-acetylpyridines. Additionally, two or more ammonia types in different forms can be mixed together for use. The mix ratio for use in mixture may appropriately be determined.

The temperature of the cyclization reaction is within a range of −20 to 200° C., preferably within a range of 50 to 120° C., more preferably within a range of 70 to 100° C. Generally, these reactions are on completion within 24 hours. In many cases, the elimination of the raw materials can be confirmed in 10 minutes to 12 hours.

In accordance with the method of the invention, not any particular catalyst is needed. For the reaction of the reaction product resulting from the reaction of 4-acetylpyridines and 3-amino-2-propenals with ammonia or an ammonium salt, however, the reaction is completed in a shorter period of time, advantageously, when an acid catalyst is used. As the acid catalyst, any acid catalysts may be used. As such acid catalyst, inorganic acids such as sulfuric acid and hydrochloric acid, organic acids such as p-toluenesulfonic acid, formic acid, acetic acid, and propionic acid, and ion exchange resins of strong acidity, such as Amberlite and Amberlist can be used. Preferable are formic acid, acetic acid and propionic acid capable of retaining the inside of the reaction system at weak acidity. More preferable is acetic acid.

In accordance with the invention, satisfactorily, the use of a reaction solvent is not essential throughout all the steps. If necessary, however, any polar solvents or non-polar solvents may be used, including for example water; aromatic solvents such as benzene, toluene, xylene, chlorobenzene, and dichlorobenzene; polar solvents such as pyridine, acetonitrile, N,N-dimethylformamide, N,N-dimethylacetamide, N-methylpyrrolidone, and dimethylsulfoxide; ester solvents such as methyl acetate, ethyl acetate and butyl acetate; alcoholic solvents such as methanol, ethanol, isopropyl alcohol, butanol, and t-butanol; ether solvents such as diethyl ether, diisopropyl ether, dibutyl ether, methyl t-butyl ether, and tetrahydrofuran. Preferable are alcoholic solvents, polar solvents, and ether solvents. More preferable are methanol, dimethylsulfoxide and tetrahydrofuran. Additionally, two or solvents can be used in mixture. In case of using solvents in mixture, the mix ratio may appropriately be determined. As to the amount of the reaction solvent, the reaction solvent is used within a range of 0.1- to 50-fold by weight, preferably 0.5- to 30-fold by weight, more preferably 1- to 10-fold by weight to 4-acetylpyridines.

The method for purifying the bipyridine derivative as the object substance after completion of the reaction includes extraction using water and an organic solvent such as ethyl acetate or toluene which can be partitioned from water, recrystallization using alcohol, hexane, toluene and the like, column purification using silica gel or alumina or the like as an immobilization bed, distillation and the like. These methods may be used singly or in combination of two or more thereof, for purification, to obtain the object substance at high purity.

The invention is now described specifically in the following Examples. However, the invention is not limited to them. Herein, the structural analysis was done by 1H-NMR and on mass spectrum.

EXAMPLE 1

Synthesis of 5-nitro-2,4'-bipyridine [(I)-1]

3-(Dimethylamino)-2-nitro-2-propenal (60.5 g) was dissolved in tetrahydrofuran (500 ml). To the resulting solution were added 4-acetylpyridine (48.5 g) and potassium t-butoxide (121.14 g), for agitation at 30° C. for 30 minutes. After ammonium acetate (185 g) and acetic acid (140 ml) were added, reaction was progressed at an inner temperature of 95° C. for 4 hours while tetrahydrofuran was distilled off. To the reaction solution was added aqueous 25% NaOH solution (400 ml), for crystallization. The resulting crystal was dried to obtain the object compound in pale dark brown crystal (58 g; yield of 72%).

EXAMPLE 2

Synthesis of 5-cyano-2,4'-bipyridine [(I)-2]

By the same method as in Example 1,5-bromo-2,4'-bipyridine was prepared. The resulting 5-bromo-2,4'-bipyridine (7.0 g) was dissolved in N,N-dimethylacetamide (15 ml), followed by addition of copper (I) cyanide (2.8 g), for agitation at 140° C. for 3 hours. After the reaction solution was cooled, aqueous 25% NaOH solution (10 ml) was added to deposit a crystal, which was filtered and recovered, to obtain the object substance (4.5 g; yield of 83%).

EXAMPLE 3

Synthesis of 5-formyl-2,4'-bipyridine [(I)-3]

5-Bromo-2,4'-bipyridine (7.0 g) obtained in the same manner as in Example 2 was dissolved in anhydrous tetrahydrofuran (50 ml), to which a 1.6 mol/L solution (20 ml) of n-BuLi in hexane was added at −70° C. or less, followed by addition of N,N-dimethylformamide (4.2 g), for agitation for 3 hours while the inner temperature was retained at −78° C. After the reaction solution was dropwise added to aqueous saturated sodium carbonate solution (200 ml), followed by extraction three times into toluene (300 ml), concentration and drying, the object substance (4.6 g; yield of 83%) was recovered.

EXAMPLE 4

5-Carboxamide-2,4'-bipyridine [(I)-4]

5-Amino-2,4'-bipyridine (6.8 g) obtained in Example 3 was added to ethyl acetate (200 ml), to which acetic anhydride (4.3 g) was added. Triethylamine (8.1 g) was dropwise added. After reflux under heating for one hour, concentration and drying, the object substance (7.8 g; yield of 92%) was obtained.

EXAMPLE 5

Synthesis of 5-amino-2,4'-bipyridine [(I)-5]

5-Nitro-2,4'-bipyridine (10 g) obtained in Example 1 was added to ethanol (400 ml). 10% Pd—C (50% wet with water) (0.14 g) was added, and then, hydrazine.monohydrate (10 g) was dropwise added, for reflux under heating for 3 hours. The reaction solution was filtered and concentrated. The resulting crystal was recrystallized in ethyl acetate, to obtain the object substance (8.13 g; yield of 95%).

EXAMPLE 6

Synthesis of 5-acetamide-2,4'-bipyridine [(I)-6]

5-Amino-2,4'-bipyridine (6.8 g) obtained in Example 5 was added to ethyl acetate (50 ml), to which acetic anhydride (8.5 g) was added. Triethylamine (16.2 g) was dropwise added, for reflux under heating for one hour. The reaction solution was concentrated. The resulting deposited crystal was obtained by filtration, and then rinsed in 10 ml of ethyl acetate, to obtain the object substance (7.8 g; yield of 92%).

Table 1 shows the physico-chemical values of the object substances obtained in Examples 1 through 6.

TABLE 1

| Examples | Melting point (° C.) | MS [M + H+] |
|---|---|---|
| 1 | 203-204 | 201 |
| 2 | 218-220 | 181 |
| 3 | 114-115 | 184 |
| 4 | 220-229 | 199 |
| 5 | 238-240 | 171 |
| 6 | 208-209 | 213 |

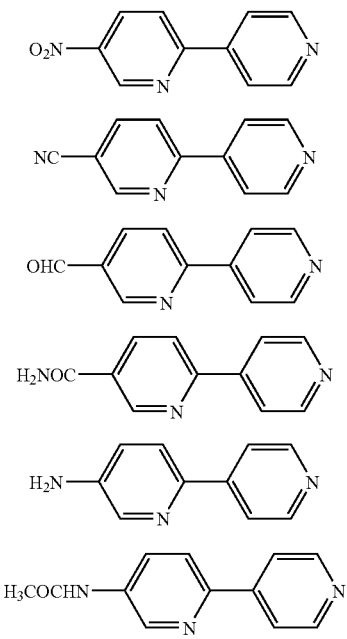

In the same manner, the following compounds were obtained.

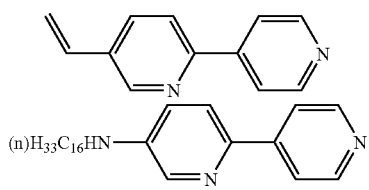

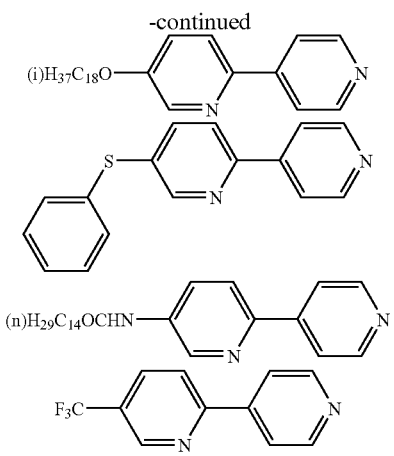

The pyridine derivatives obtained in accordance with the invention are useful as intermediates for pharmaceutical products, agricultural chemicals, electrophotographic photosensitive materials, dyes and the like.

What is claimed is:

1. A bipyridine compound represented by the general formula (I) or a salt thereof:

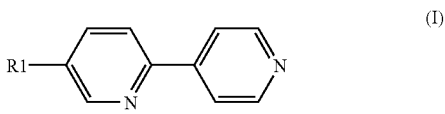

wherein R1 represents an alkyl group with 2 to 20 carbon atoms having a substituent, an alkylthio group with 1 to 20 carbon atoms, which may have a substituent, substituted or unsubstituted aminomethyl group, trifluoromethyl group, substituted or unsubstituted thiomethyl group, substituted or unsubstituted alkenyl group, substituted or unsubstituted alkoxy group, substituted or unsubstituted aryloxy group, unsubstituted carbamoyl group, unsubstituted or monosubstituted sulfamoyl group, substituted or unsubstituted thiol group, unsubstituted or monosubstituted amino group, substituted carbonylamino group, substituted or unsubstituted ureido group, nitro group, cyano group, formyl group, iodine atom or fluorine atom.

2. The bipyridine compound or a salt thereof according to claim 1, wherein R1 represents an alkyl group with 2 to 20 carbon atoms having a substituent, an alkoxy group with 1 to 20 carbon atoms, which may have a substituent, an alkylthio group with 1 to 20 carbon atoms, which may have a substituent, unsubstituted or monosubstituted amino group, nitro group, formyl group, cyano group, unsubstituted carbamoyl group or substituted carbonylamino group.

3. The bipyridine compound or a salt thereof according to claim 1, wherein R1 represents unsubstituted amino group, nitro group, formyl group, cyano group, unsubstituted carbamoyl group or carbonylamino group substituted with a lower alkyl group.

* * * * *